DEFENSIVE PUBLICATION

UNITED STATES PATENT AND TRADEMARK OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent and Trademark Office makes no assertion as to the novelty of the disclosed subject matter.

PUBLISHED JUNE 1, 1976

947 O.G. 13

T947,006

MODIFIED CRACKING OF PARAFFINS

David V. Porchey, Dennis Jack Royer, and Charles M. Starks, Ponca City, Okla., assignors to Continental Oil Company, Ponca City, Okla.

Continuation of abandoned application Ser. No. 489,958, July 19, 1974. This application July 28, 1975, Ser. No. 599,564

Int. Cl. C07c *3/30*

U.S. Cl. 260—683 R

No Drawing. 12 Pages Specification

In a process for cracking normal paraffins containing from about 2 to about 10 carbon atoms to alkenes, the instant invention relates to an improvement comprising admixing about 0.1 to about 70 percent by weight of $H_2Se$ or $H_2Te$ (or an amount of a compound which yields a SeH or a TeH radical in the cracking environment sufficient to yield that amount of SeH or TeH) based on the hydrocarbon stream containing the paraffins and the paraffin to be cracked and then passing the resulting mixture through a reactor maintained at a temperature of about 900° F. to about 2000° F. with a residence time of about 0.01 to about 20 seconds and a pressure of about 0 to about 5000 p.s.i.g. Steam is also employed.